US007235075B1

(12) United States Patent
Metz-Stavenhagen

(10) Patent No.: US 7,235,075 B1
(45) Date of Patent: Jun. 26, 2007

(54) ANCHORING ELEMENT FOR SECURING A ROD ON A VERTEBRA

(76) Inventor: Peter Metz-Stavenhagen, Schlossstrasse 24, Bad Wildungen (DE) D-34537

( * ) Notice: Subject to any disclaimer, the term of this patent is extended or adjusted under 35 U.S.C. 154(b) by 85 days.

(21) Appl. No.: 10/515,047

(22) PCT Filed: May 19, 2003

(86) PCT No.: PCT/DE03/01610

§ 371 (c)(1),
(2), (4) Date: Nov. 19, 2004

(87) PCT Pub. No.: WO03/096916

PCT Pub. Date: Nov. 27, 2003

(30) Foreign Application Priority Data

May 21, 2002 (DE) .......................... 202 07 850 U
May 21, 2002 (DE) .......................... 202 07 852 U

(51) Int. Cl.
*A61B 17/70* (2006.01)
(52) U.S. Cl. ....................................... 606/61
(58) Field of Classification Search ................. 606/61, 606/72, 73
See application file for complete search history.

(56) References Cited

U.S. PATENT DOCUMENTS

| 6,077,262 | A  | * | 6/2000 | Schlapfer et al. ............ 606/61 |
| 6,224,598 | B1 |   | 5/2001 | Jackson |
| 6,251,112 | B1 |   | 6/2001 | Jackson |
| 6,258,090 | B1 | * | 7/2001 | Jackson ....................... 606/61 |
| 6,755,829 | B1 | * | 6/2004 | Bono et al. .................. 606/61 |
| 6,786,903 | B2 | * | 9/2004 | Lin .............................. 606/23 |
| 2002/0068938 | A1 | * | 6/2002 | Jackson ....................... 606/61 |

FOREIGN PATENT DOCUMENTS

| DE | 92 02 745 U1 | 6/1992 |
| DE | 94 02 839 | 5/1994 |
| DE | 297 10 484 | 11/1998 |
| EP | 0 885 598 | 12/1998 |
| EP | 1 064 885 A | 1/2001 |
| EP | 1064885 A1 * | 1/2001 |
| EP | 1 190 678 A | 3/2002 |
| WO | WO 95/01132 | 1/1995 |

* cited by examiner

*Primary Examiner*—Eduardo C. Robert
*Assistant Examiner*—Nicholas Woodall
(74) *Attorney, Agent, or Firm*—Thomas R. Vigil; Pyle & Piontek

(57) ABSTRACT

An anchoring element for fastening a rod of a device for adjusting a human or animal spine to a vertebral bone, and having a holding device that is substantially U-shaped and includes two substantially parallely disposed holding ridges, a rod receiving slot being formed therein, and a securing element acting against the rod accommodated in the receiving slot. The securing element includes a locking element and a ring element and the ring element is mountable to the free end of the holding ridges by means of a single turn coupling system. Further a partial thread can be provided on opposing sides of the holding ridges and two opposing thread portions and two opposing entrance portions can be configured on the circumference of the ring element the diameter of the securing element in the region of the entrance portions not exceeding the core diameter of the thread portion so that the thread portions are engageable with the partial threads of the holding ridges and the thread portions and the partial threads comprise buttress threads.

9 Claims, 11 Drawing Sheets

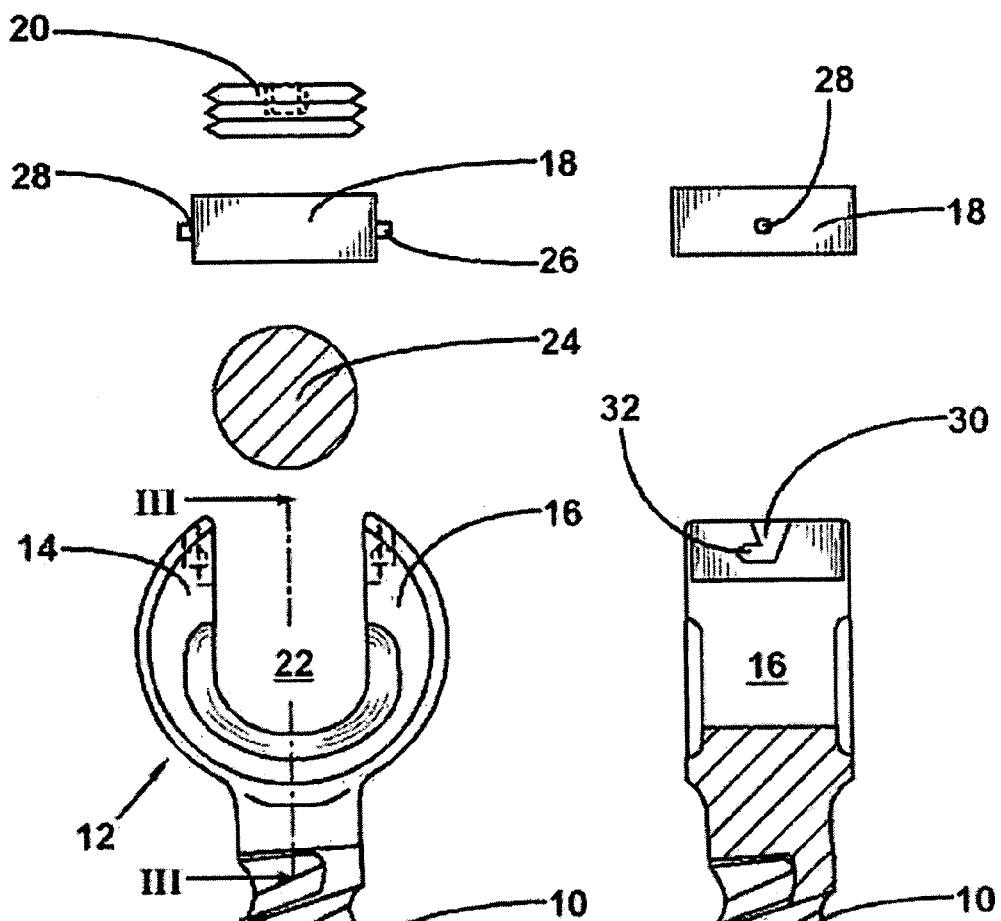
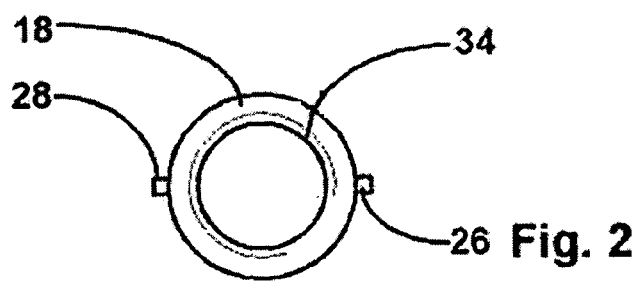
Fig. 1
Fig. 2
Fig. 3

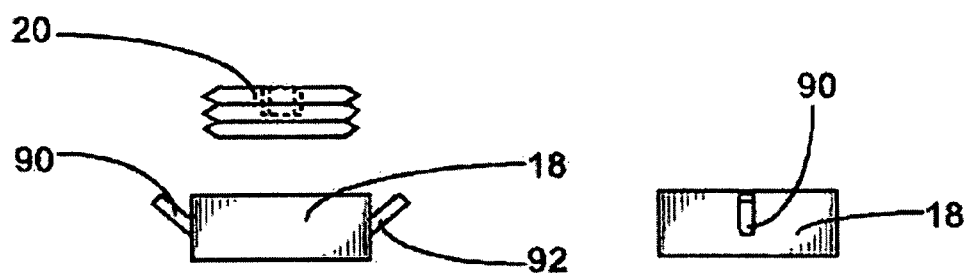
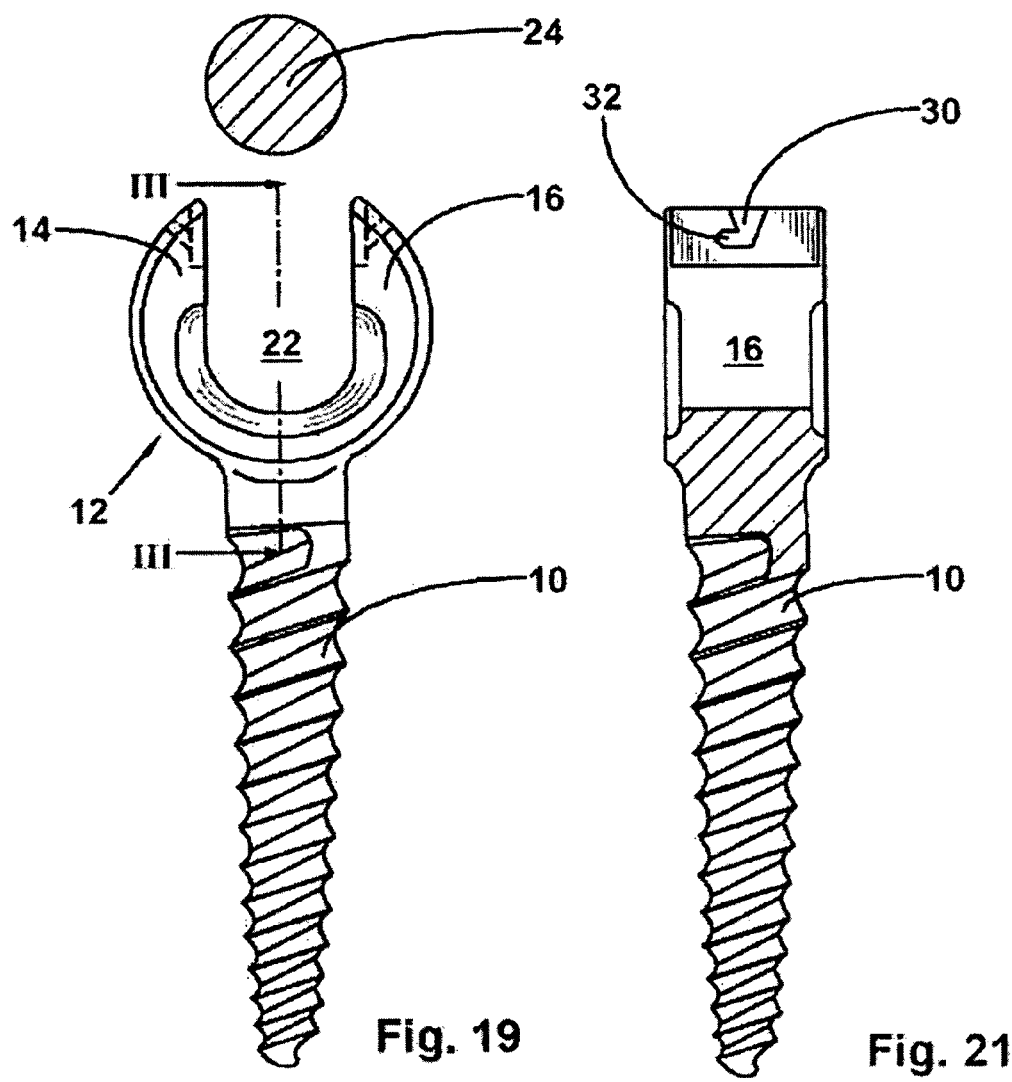
Fig. 19
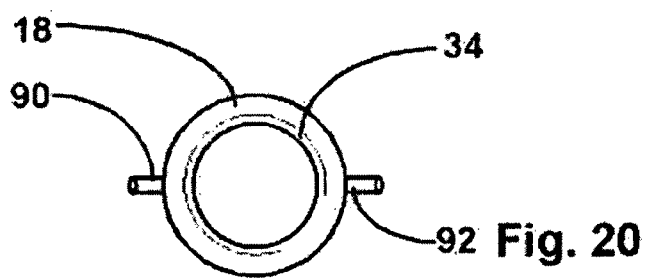
Fig. 20
Fig. 21

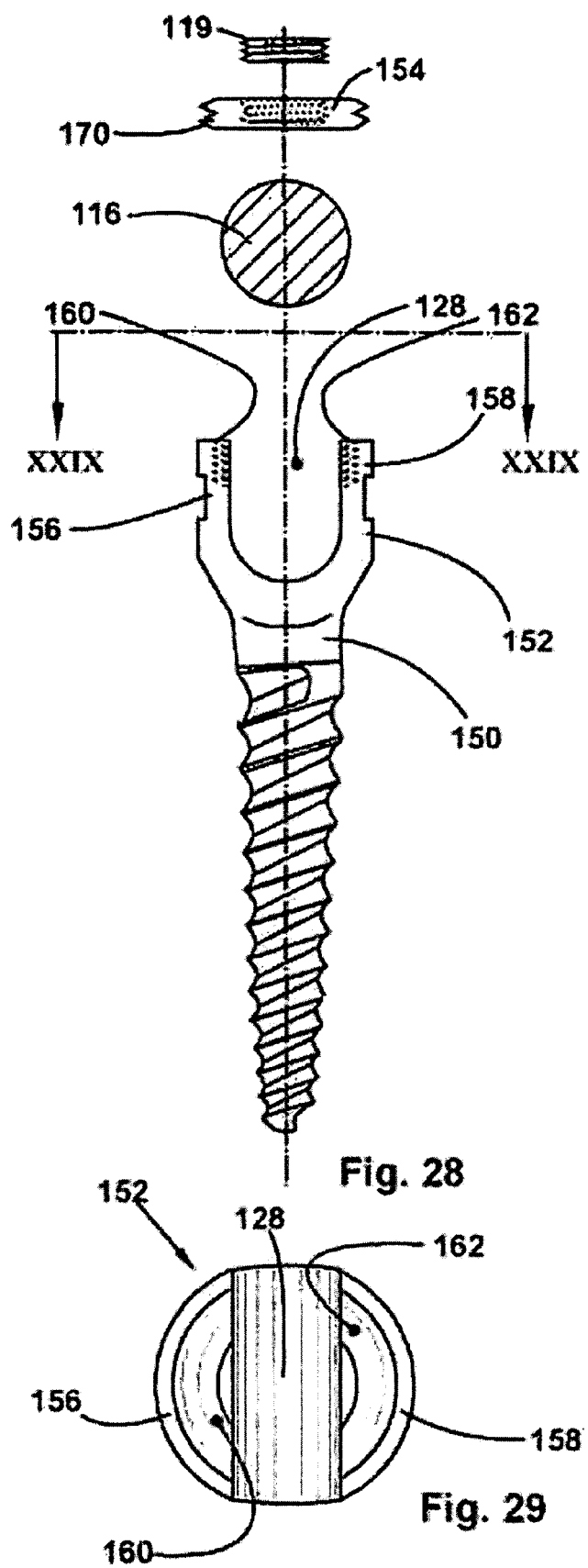
Fig. 28
Fig. 29
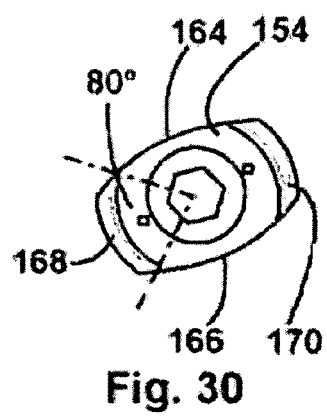
Fig. 30

ANCHORING ELEMENT FOR SECURING A ROD ON A VERTEBRA

BACKGROUND OF THE INVENTION

DE 202 07 852.3 dated May 21, 2002 and DE 202 07 850.7 dated May 21, 2002

1. Field of the Invention

The present invention relates to an anchoring element for fastening a rod of a device for adjusting a human or animal spine to a vertebral bone, said anchoring element having a holding device that is substantially U-shaped and includes two substantially parallely disposed holding ridges, a rod receiving slot being formed therein, and a securing element acting against the rod accommodated in the receiving slot.

2. Description of the Prior Art

A pedicle screw the threaded shank of which is anchorable within a vertebral bone and which comprises at its end protruding from the vertebral bone a U-shaped holding device having two parallely oriented holding ridges is known from DE 94 02 839. Between the holding ridges there is formed a slot for receiving a distraction or compression rod that can be secured and fixed by means of a securing element which is fastenable to the free ends of the holding ridges. In a first embodiment, said securing element is composed of a hexagonal ring-shaped element having a locking screw embedded therein, the entire securing element being slidable into a corresponding groove provided in the holding ridges. The securing element straddles the receiving slot so that the locking screw acts directly onto the rod to fix it.

In another embodiment, the securing element is composed of a sleeve with internal thread surrounding the holding element, said sleeve being screwable onto a mating thread provided on the outer sides of the holding ridges so that the locking screw provided on the front side of the sleeve is allowed to engage into the receiving slot in order to fix the rod.

In such a device the pedicle screw must first be anchored within the vertebral body and then the rod is placed into the receiving slot. Next, and prior to bringing the vertebra or the rod into the desired position by tightening the locking screw, the securing element is either inserted into the grooves or screwed onto the holding device. It has been found that this is very difficult to carry out in practice because both inserting the securing element into the grooves and screwing the securing element onto the holding device require great dexterity, the vertebral body and/or the rod concurrently having to be prevented from coming out of place in the meantime.

An anchoring element having holding ridges on the inner sides of which there is provided a buttress thread for receiving the locking screw is known from DE 297 10 484. This feature permits to eliminate the forces which, in the case of a normal thread, act radially onto the holding ridges so that only axially acting forces are applied onto the holding ridge. As a result, the holding ridges are prevented from being bent apart so that the ring element surrounding the holding ridges may also be absent. In this case also, it has been found very tedious to screw the respective one of the locking screws into the corresponding buttress thread while maintaining the spine and/or the rod in the desired position until the locking screw takes hold of the rod by itself.

The term buttress thread is meant to include, besides the buttress metric thread DIN 513, buttress threads having a slightly larger or slightly smaller flank angle, a flank angle of 0° or a negative flank angle as well as buttress threads in accordance with EP 885 598.

An anchoring element also comprising a pedicle screw with U-shaped holding ridges integrally formed therewith is known from WO 95/01132. Pins directed toward the inside of the U-shape are formed integrally with said holding ridges. Said anchoring element further includes a flange-shaped securing element on the top side of which there is formed a protruding circumferential collar and on the bottom side of which there are provided two angled grooves for inserting said securing element into the pins of the holding elements. The securing element further includes an internal thread into which a grub screw is screwable for fixing the rod.

During surgery, the pedicle screw is first inserted into the corresponding site in the bone before the fixation rod is caused to enter the U-shaped holding device. Due to the little space available within the U-shaped holding device, the pin can only be designed very small on the inner side of the holding ridges. For this reason, it is very difficult for the surgeon, upon insertion of the fixation rod, to place with aiming accuracy the securing element onto said pins and to pivot it. This operation is rendered even more difficult by the fact that the surgeon cannot see the pin, which is concealed, while inserting the securing element into the U-shaped holding device. In this case as well, the fixation rod is first roughly held by the securing element prior to being fixed in its final position by the grub screw.

A pedicle screw the threaded shank of which is anchorable within a vertebral bone and which comprises at its end protruding from the vertebral bone a U-shaped holding device having two parallely oriented holding ridges is known from DE 92 02 745 U1. Between the holding ridges there is formed a slot for receiving a distraction or compression rod that can be secured and fixed by means of a securing element which is fastenable to the free ends of the holding ridges. Said securing element is configured to be a grub screw and engages in corresponding thread portions disposed on the respective one of the internal sides of the holding ridges. For actuating the grub screw, a recess for receiving a hexagonal wrench is formed at its upper front side.

U.S. Pat. No. 6,224,598 B1 discloses an anchoring element for fastening a rod to a spine that is also composed of a pedicle screw, a U-shaped holding device integrally formed therewith and a locking element. Here, the locking element is made of two parts, an outer part being configured to be a sleeve having both an internal and an external thread and an inner part being formed like a bolt and comprising a thread on its one end and a hexagon nut on the other end. The sleeve is thereby screwed by hand into the thread of the holding element, temporarily retaining the fixation rod. Next, the bolt is screwed into the sleeve until the thread of the bolt has completely disappeared in the sleeve. Upon screwing the bolt further down, it carries the sleeve along and both parts are moved toward the fixation rod to reliably make it fast.

In such type devices, the pedicle screw must first be screwed into the vertebral body and then the rod may be placed into the receiving slot. The grub screw is then screwed into the holding device to loosely retain the rod. Next, the vertebral body is brought into the desired position by setting the rod before the grub screw is firmly tightened to fix the rod in this position. The rod may thereby be configured as a distraction, a compression or a connection rod for example.

BRIEF SUMMARY OF THE INVENTION

In view thereof, it is the object of the present invention to provide an anchoring element the securing element of which is easy and fast to fit in and reliably absorbs the forces generated.

As a technical solution to this problem, an anchoring element having the feature of claim 1 or the feature of claim 13 is proposed in accordance with the invention. Advantageous developed implementations will become apparent in the subordinate claims.

An anchoring element having a holding device that is substantially U-shaped and includes two substantially parallely disposed holding ridges, a rod receiving slot being formed therein, and a securing element acting against the rod accommodated in the receiving slot, the securing element including a locking element (20, 50) and a ring element (18, 48), and the ring element (18, 48) being mountable to the free end of the holding ridges (14, 16, 44, 46) by means of a single turn coupling system, has the advantage that the ring element needs only to be placed axially onto the free ends of the holding ridges and can be brought into its final secured position by slightly pivoting it. A thus secured ring element already retains the rod located in the receiving slot temporarily in the desired position so that the operating surgeon is now allowed to screw the locking screw in his own time to adjust and fix the rod It has thereby been found advantageous to configure the single turn coupling system as a bayonet coupling having a radially projecting gripper and a slot-type or a groove-type recess, said gripper engaging in the receiving recess to fix the ring element of the holding ridges. Such a bayonet coupling can be manufactured at low cost and allows for fast and easy mounting of the ring element on the holding device of the anchoring element.

Designing the receiving recess with an axial entrance and with a radial holding element has the advantage that the gripper can easily be brought into the entrance and by rotation into the holding element where it remains and forms an interlocking bayonet coupling.

It is understood that the rod can be configured to be a distraction rod, a compression rod or a connection rod for example.

In a preferred embodiment, the ring element is insertable into the receiving slot and mountable between the holding ridges, the gripper being mounted outside on the ring element whilst the receiving recess is disposed in the holding ridges. This has the advantage that the ring element is thus also integrated in the receiving slot so that the entire anchoring element can be implemented with very small dimensions.

In another preferred embodiment, the ring element forms a grip around the holding ridges, the receiving recess being disposed in the ring element, whilst the gripper is mounted on the holding ridges. This has the advantage that the radial forces originating from the locking element are thus also absorbed by the ring element without the holding ridges being undesirably urged apart.

In still another preferred embodiment, the entrance is V-shaped. The advantage thereof is that the gripper which has to be inserted into this entrance can be roughly placed into said entrance, since, thanks to the V-shape configuration, it is still guided correctly to the transversely oriented holding element prior to being inserted into the ring element by pivoting the latter. This makes placement of the ring element onto the holding ridges even easier.

In still another preferred embodiment the holding element is configured to extend upward so that the ring element is constrained to not only execute a rotation but in addition thereto an axial movement for its release. Such an additional requisite for releasing the ring element makes inadvertent release of the ring element more difficult. The same applies in a similar fashion for a wider end of the holding element.

In still another preferred embodiment the gripper is configured as a pin or a flank. Advantageously, the flank rests against the holding element by a larger surface so that inadvertent release of the ring element is rendered more difficult as a result of the thus increased friction.

In still another preferred embodiment the gripper extends through the receiving recess and protrudes therefrom and is curved or inclined, preferably in the direction of the forces applied onto the securing element, in such a manner that the holding ridge is pushed inward. As a result thereof, the holding ridges are pushed inward under the action of the forces holding the anchoring element and it is made certain that the ring element is reliably retained in the holding ridges. The securing element is thus prevented from springing out when the holding ridges are being bent.

In a preferred developed implementation, a thread for receiving the locking element is provided in the ring element. Beside the advantage of a small overall size mentioned herein above, this offers the further advantage that the radial forces originating from the locking element are completely absorbed by the ring element without deformations as they are known from prior art.

An anchoring element having a holding device that is substantially U-shaped and includes two substantially parallely disposed holding ridges, a rod receiving slot being formed therein, and a securing element acting against the rod accommodated in the receiving slot, the holding ridges comprising a partial thread on opposing sides, the securing element including a locking element and a ring element, two opposing thread portions and two opposing entrance portions being configured on the circumference of the ring element, the diameter of the securing element in the region of the entrance portions not exceeding the core diameter of the thread portion so that the thread portions are engageable with the partial threads of the holding ridges, has the advantage that the securing element with its ring element needs only be oriented in such a manner that its insertion portions are confronting the holding ridges and that the securing element must then be inserted axially into the holding device to then, with, for example, a one-quarter rotation, cause the threaded portions of the ring element to engage with the partial threads of the holding ridges. Finally, the locking element is tightened to fix the rod. As a result, the securing element may easily and quickly be placed into the holding device and fixed therein.

It has been found advantageous to configure the thread portions and the partial threads to be buttress threads so that the holding ridges are not urged apart by the action of the forces.

To allow for easy axial insertion of the securing element in the holding device, it has been found advantageous to extend each thread portion over a circular segment of preferably 60°, at the most however over a circular segment of slightly short of 90°. As a result, the free portion of the ring element as viewed over the circumference is larger than the portion provided with a thread portion so that the ring element being axially inserted into the holding device needs not be oriented very precisely.

In another preferred embodiment the ribs of the threaded portion are configured on at least one front side to be chamfered, rounded or flattened so that the rib of the thread may be easily inserted into the partial thread. It has been found advantageous that thus configured front sides of the rib need at first only be roughly inserted into the partial thread, with said front sides being automatically pulled into their correct position.

Further advantages of the anchoring element of the invention will become apparent in the appended drawings and in the following description of embodiments thereof. Likewise, the above mentioned features and those described herein after may be used alone or in any combination with each other within the scope of the present invention. The embodiments discussed herein are merely exemplary in nature and are not intended to limit the scope of the invention in any manner.

BRIEF DESCRIPTION OF THE SEVERAL VIEWS OF THE DRAWING

In the drawing:

FIG. 1 is an exploded view of a first embodiment of an anchoring element of the invention with a rod;

FIG. 2 is a top view of the ring element of FIG. 1;

FIG. 3 is a partial sectional side view of the anchoring element of FIG. 1, taken along the line III-III of FIG. 1;

FIG. 19 is an exploded view of a seventh embodiment of an anchoring element of the invention;

FIG. 20 is a top view of the ring element of FIG. 19;

FIG. 21 is a side view of the anchoring element of FIG. 19;

FIG. 28 is an exploded view of a ninth embodiment of an anchoring element of the invention with a rod.

FIG. 29 is a top view of the holding device of the anchoring element of FIG. 28;

FIG. 30 is a top view of the securing element of the anchoring element of FIG. 28.

DETAILED DESCRIPTION OF THE INVENTION

Figure 4:
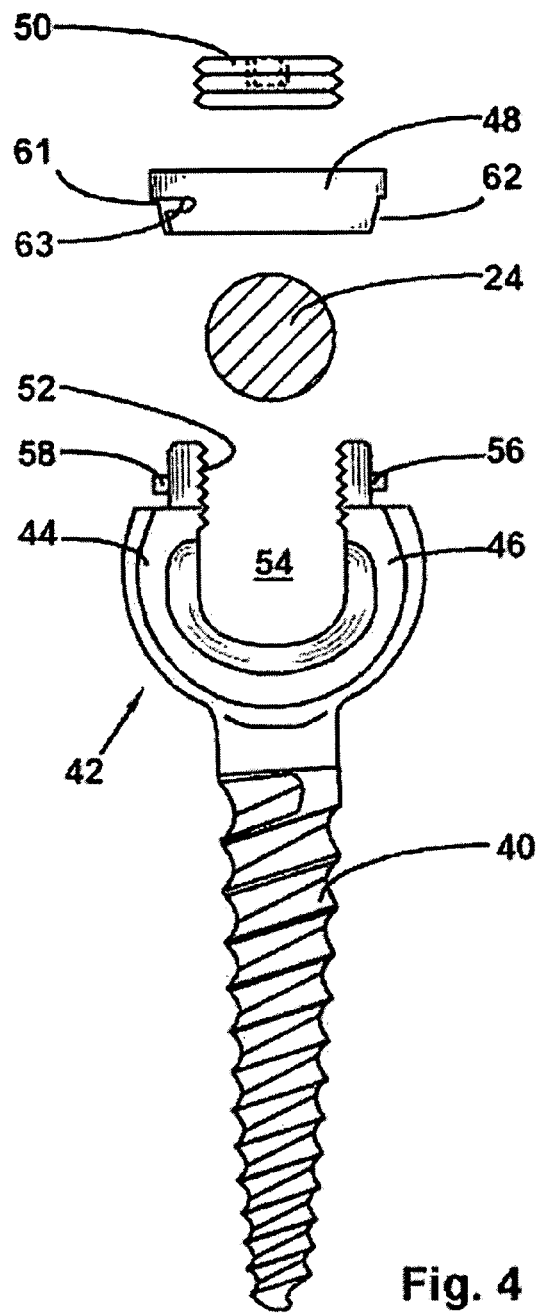
FIG. 4 is an exploded view of a second embodiment of an anchoring element of the invention with a rod.

The FIGS. 1 to 3 illustrate a first embodiment of an anchoring element for insertion into the vertebral bone that is configured to be a pedicle screw, said anchoring element including a threaded shank 10 as well as a U-shaped holding device 12 having two substantially parallely disposed holding ridges 14, 16, a ring element 18 and a locking element 20 implemented in the form of a grub screw. In the holding device 12 there is provided a receiving slot 22 for receiving a rod 24 that is fixed by the securing element consisting of the locking element 20 and the ring element 18.

In this embodiment, two bayonet pins 26, 28 are formed on opposing sides of the ring element 18 so as to project radially, said pins being insertable into a corresponding entrance 30 formed on the inner side of the holding ridges 14, 16 and into a holding element 32. The ring element 18 is inserted from the top by its two pins 26, 28 into the entrance 30 which is open toward the top and is pushed down to the bottom of the entrance 30 before the ring element 18 is pivoted by some angle degrees so that the pins 26, 28 are brought to the end of the holding elements 32. Once this position has been reached, the ring element 18 is released and reliably remains in this position.

As best shown in FIG. 3, the entrance 30 is of a V-configuration type, thus forming a large catch area for insertion of the pins 26, 28.

In the ring element 18 there is provided an internal thread 34 for receiving the locking element 20 configured to be a grub screw. The locking element 20 is thereby screwed into the ring element 18 until the locking element 20 exerts a pressure onto the rod 24 and fixes it in the desired position.

Figure 6:
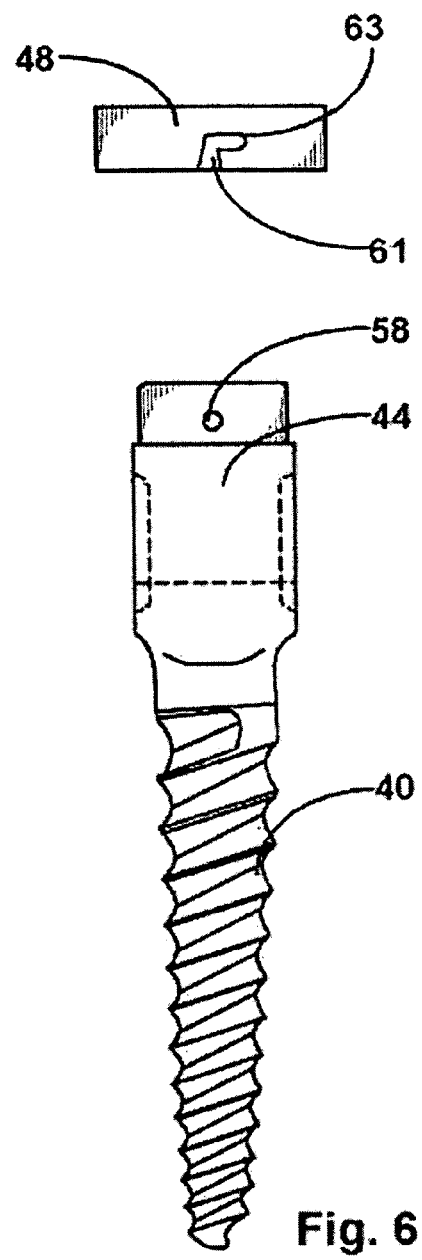
FIG. 6 is a side view of the anchoring element of FIG. 4.
Figure 5:
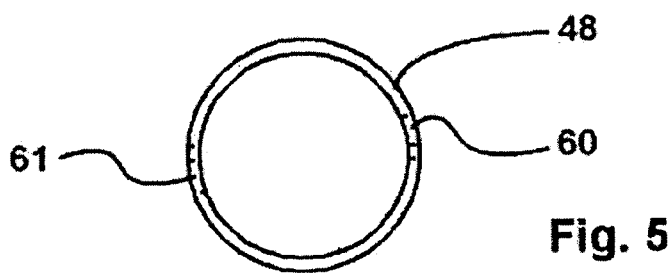
FIG. 5 is a top view of the ring element of FIG. 4.

The FIGS. 4 to 6 illustrate a second embodiment of an anchoring element of the invention that is also configured to be a pedicle screw. Again, said anchoring element is composed of a threaded shank 40 for mounting the anchoring element in the vertebral bone, of a U-shaped holding device 42 having two substantially parallely disposed holding ridges 44, 46, a ring element 48 and a locking element 50 implemented in the form of a grub screw. In this embodiment, an internal thread 52 for receiving the locking element 50 configured to be a grub screw is formed on the respective inner sides of the holding ridges 44, 46. In order to prevent the radial forces acting onto the holding ridges 44, 46 from causing the holding ridges 44, 46 to bend apart in this embodiment, the ring element 48 is placed outside of and around the holding ridges 44, 46.

In this embodiment also, a rod 24 receiving slot 54 is formed in the holding device 42, said rod being locked in the desired position by the locking element 50.

A radially projecting pin 56, 58 is provided on the sides of the holding ridges 44, 46 facing outward, said pins being insertable into corresponding entrances 61, 62 provided on the inner side of the ring element 48, mating holding elements 62, 63 being almost perpendicularly adjoined to the entrance 60, 61 in this case as well. Again, the entrances 60, 61 are of a V-type configuration to form a large catch area.

Figures 7, 9:
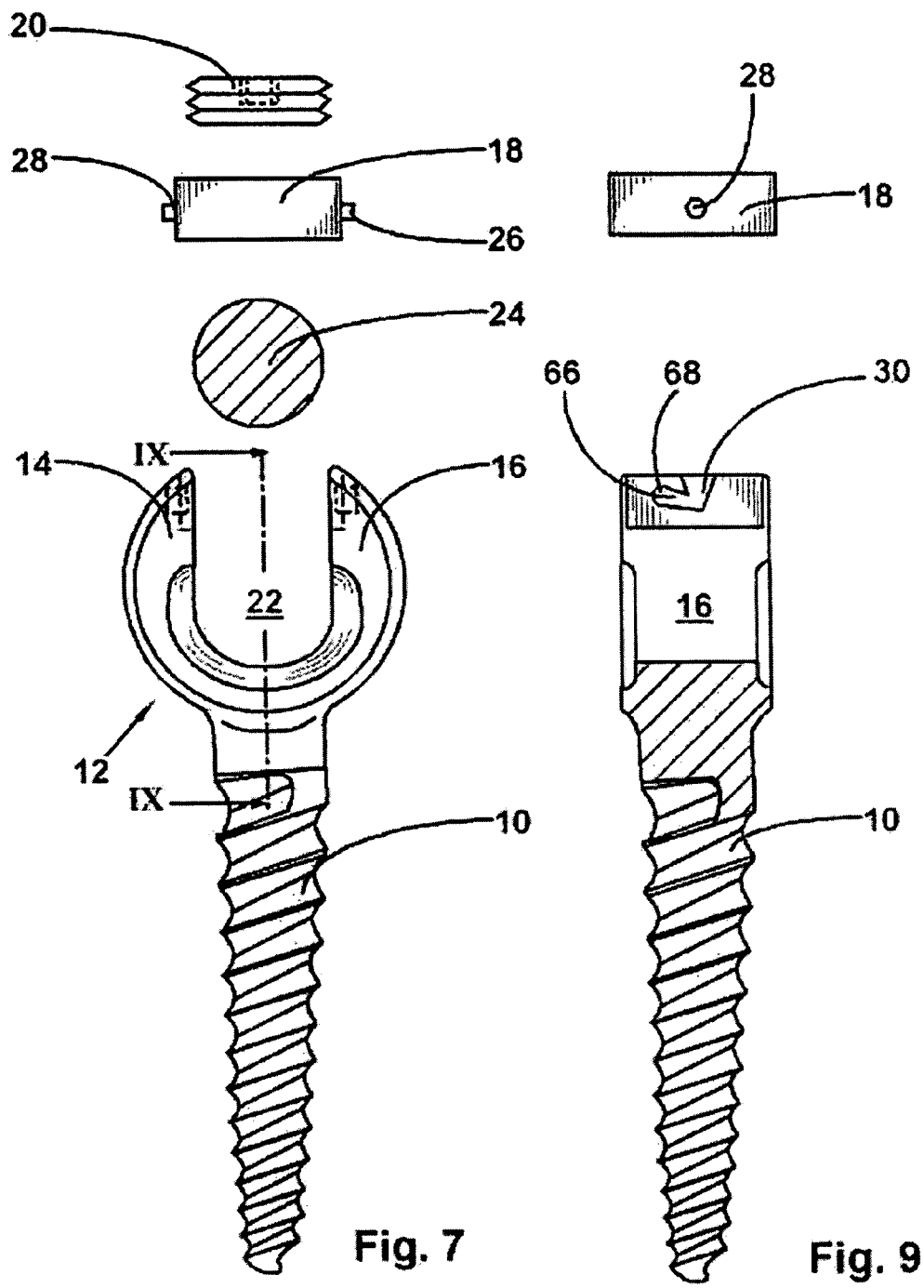
FIG. 7 is an exploded view of a third embodiment of an anchoring element of the invention with a rod.
FIG. 9 is a partial sectional side view of the anchoring element of FIG. 7, taken along the line IX-IX of FIG. 7.
Figure 8:
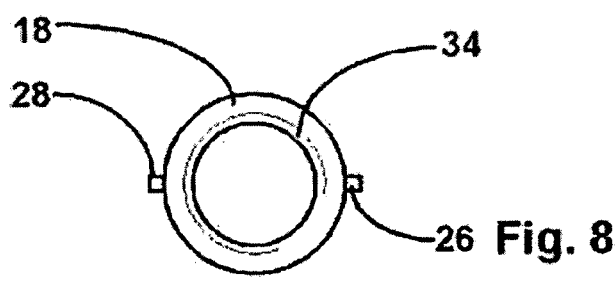
FIG. 8 is a top view of the ring element of FIG. 7.

The FIGS. 7 to 9 illustrate a third embodiment of an anchoring element of the invention that is also configured to be a pedicle screw. This third embodiment differs from the first embodiment in accordance with the FIGS. 1 to 3 in that a holding element 66 that extends slightly upward and is adjoined to the entrance 30 is formed on the inner side of the holding ridges 14, 16, said holding element 66 having a widened portion 68 at its end. The widened portion 68 is designed to be substantially circular in shape. The pin 26 is insertable into this holding element 66 and gets jammed in the holding element 66 extending upward when the ring element 18 is rotated accordingly so that a clamped securement is achieved. The holding element 66 thereby extends upward in the direction of the forces acting on the securing element.

The widened portion 68 at the end of the holding element 66 also effects that the tension that has built up upon rotation of the ring element 18 between the pin 26, 28 or the ring element 18 on the one side and the holding ridges 14, 16 on the other side decreases at least partially thereafter since the widened portion 68 extends partially in the direction of the holding force, thus at least partially eliminating the pressure between the securing element and the rod 24. This permits to concurrently achieve reliable and permanent securement of the ring element 18 as this very pressure has to be built up again for releasing the ring element 18, which is not possible without selectively applying a force from the outside. This means that the ring element 18 cannot be released by itself.

Figure 10:
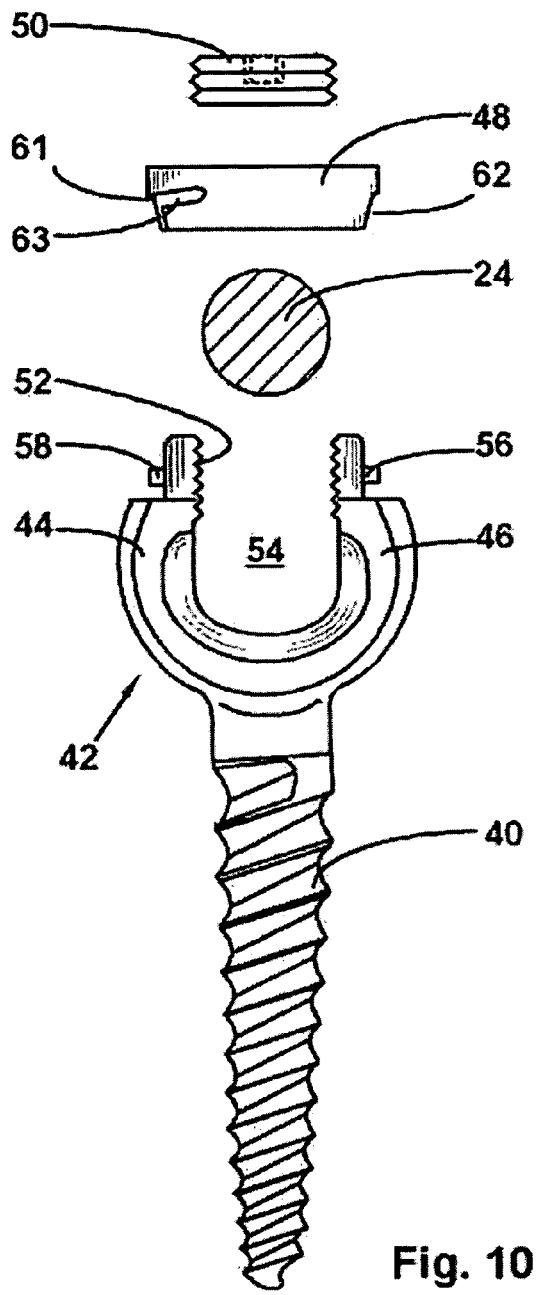
FIG. 10 is an exploded view of a fourth embodiment of an anchoring element of the invention with a rod.
Figure 12:
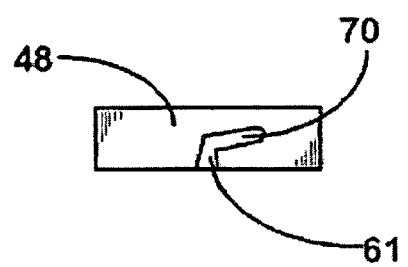
FIG. 12 is a side view of the anchoring element of FIG. 10.
Figure 12:
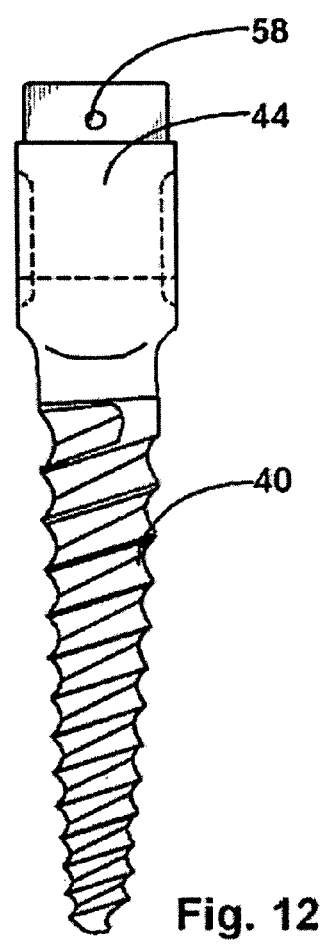
Figure 11:
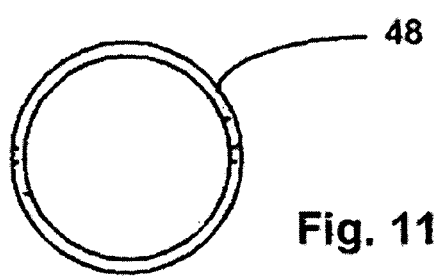
FIG. 11 is a top view of the ring element of FIG. 10.

The FIGS. 10 to 12 illustrate a fourth embodiment of an anchoring element of the invention that is also configured to be a pedicle screw. This fourth embodiment differs from the second embodiment in accordance with the FIGS. 4 to 6 in that a holding element 70 extending slightly upward and adjoined to the entrance 61 is formed on the inner side of the ring element 48. The pin 56, 58 is insertable into this holding element 70 and gets jammed in the holding element 70 extending upward when the ring element 48 is rotated accordingly so that a clamped securement is achieved.

In an embodiment not here presented the end of the holding element 70 is configured to be wider in a manner analogous to the holding element 66 of FIG. 9.

Figure 13:
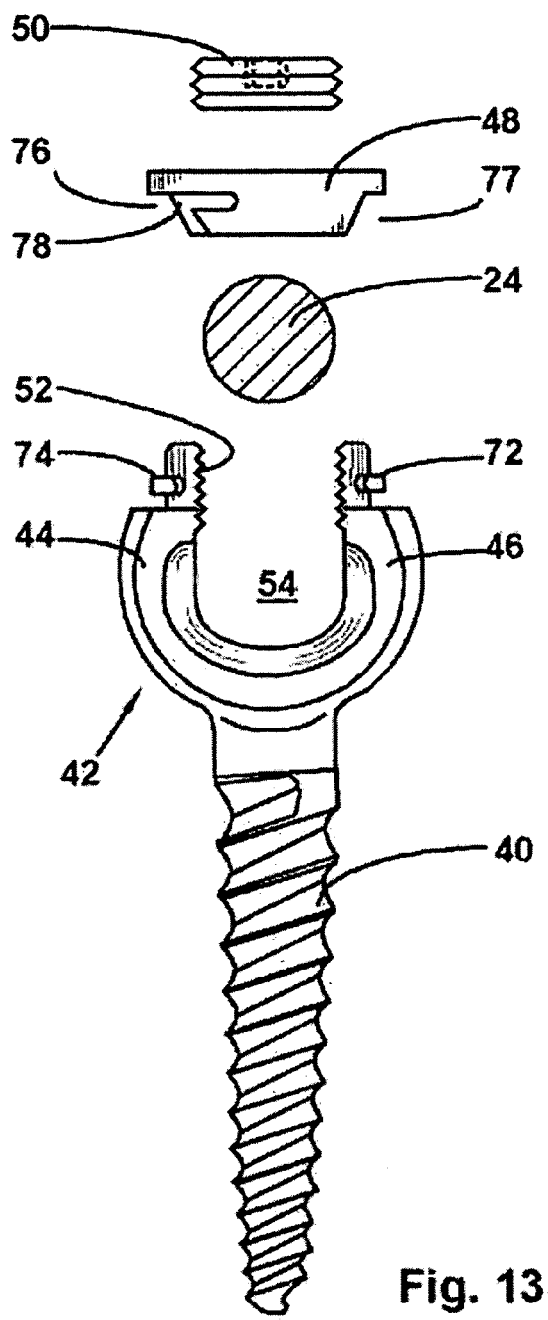
FIG. 13 is an exploded view of a fifth embodiment of an anchoring element of the invention with a rod.
Figure 15:
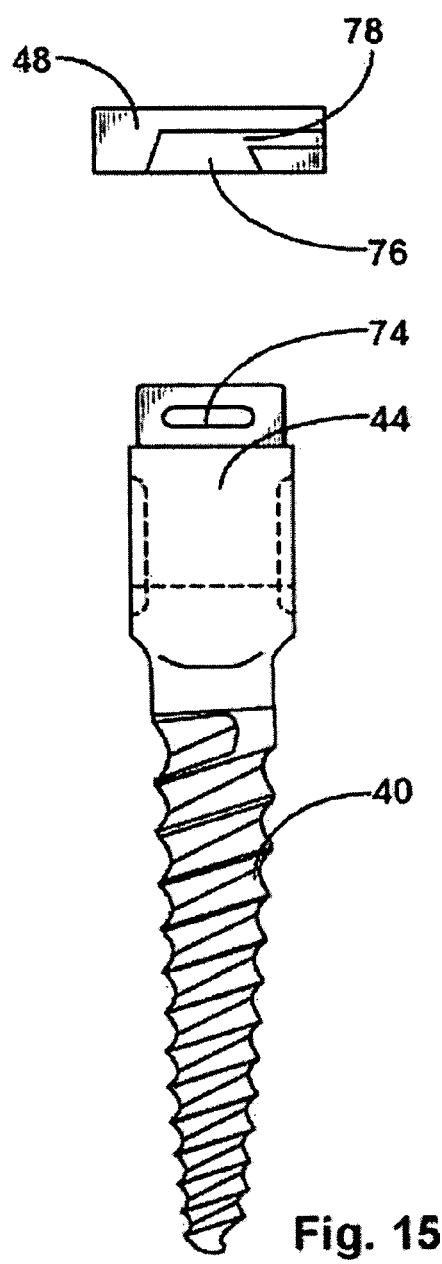
FIG. 15 is a side view of the anchoring element of FIG. 13.
Figure 14:
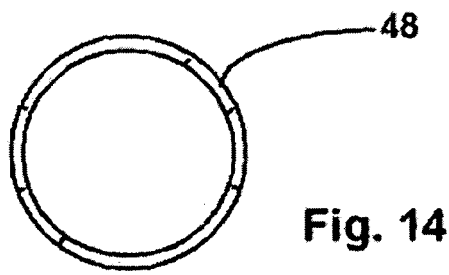
FIG. 14 is a top view of the ring element of FIG. 13.

The FIGS. 13 to 15 illustrate a fifth embodiment of an anchoring element of the invention that is also configured to be a pedicle screw. This fifth embodiment differs from the second embodiment in accordance with the FIGS. 4 to 6 in that here the gripper is configured to be a bayonet flank 72, 74 that is insertable into a corresponding entrance 76, 77 and holding element 78 provided on the ring element 48. This wide flank 72, 74 offers a large contact surface between ring element 48 and holding ridge 44, 46, which results in high friction when the ring element 48 is properly positioned. Said friction in turn impedes inadvertent release of the ring element 48 thus providing securement against inadvertent release of the ring element 48.

Figures 16, 17, 18:
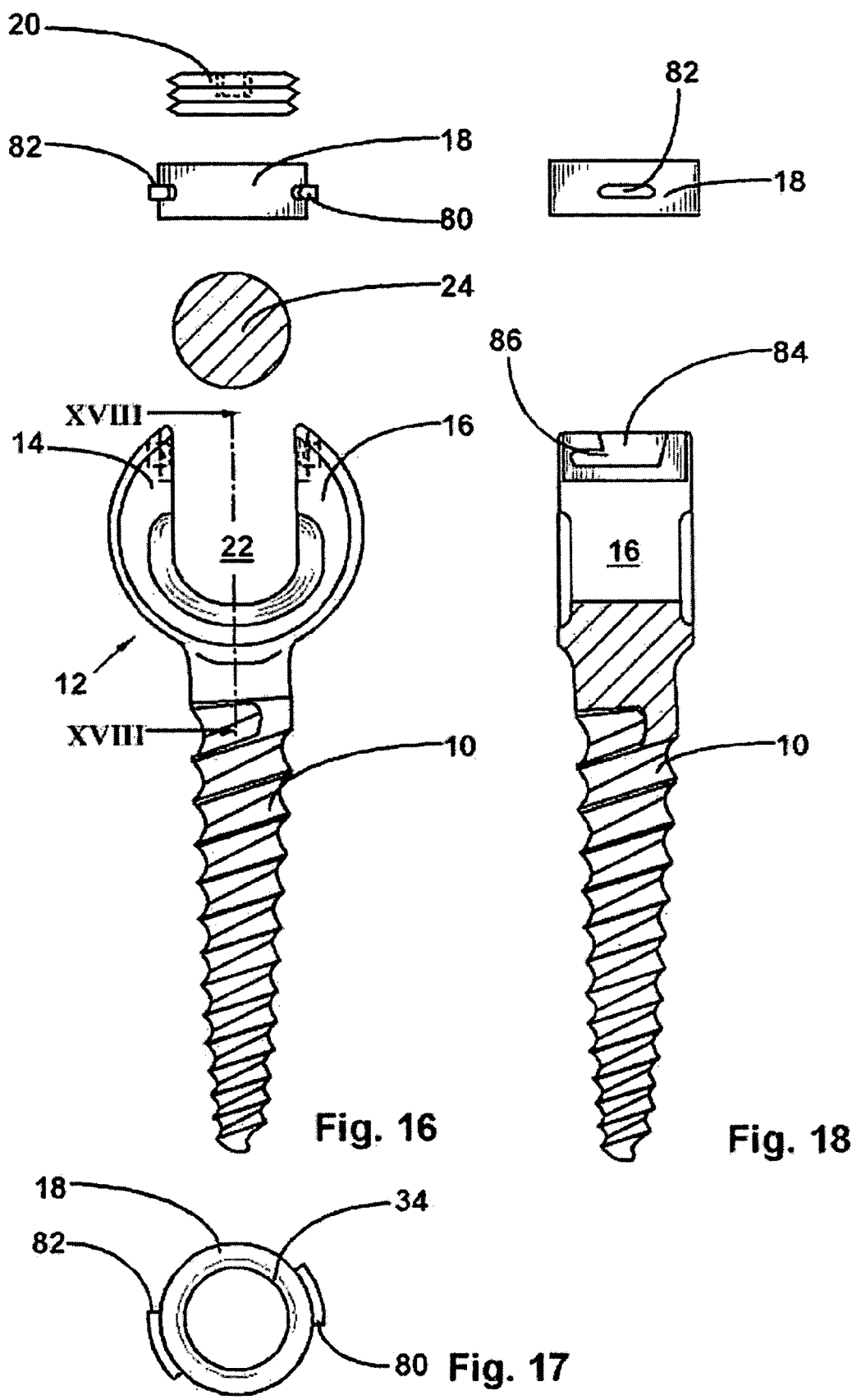
FIG. 16 is an exploded view of a sixth embodiment of an anchoring element of the invention with a rod.
FIG. 17 is a top view of the ring element of FIG. 16.
FIG. 18 is a partial sectional side view of the anchoring element of FIG. 16, taken along the line XVIII-XVIII of FIG. 16.

The FIGS. 16 to 18 illustrate a sixth embodiment of an anchoring element of the invention that is also configured to be a pedicle screw. This sixth embodiment differs from the first embodiment in accordance with the FIGS. 1 to 3 in that here as well the pins have been replaced by flanks 80, 82 engaging into a corresponding entrance 84 and holding element 86. For the rest, what has been said with respect to the fifth embodiment applies in analogous fashion.

The seventh embodiment of an anchoring element of the invention illustrated in the FIGS. 19 to 21 substantially corresponds to the first embodiment shown in the FIGS. 1 to 3 but for the gripper of the bayonet coupling, which is configured differently. As can be seen from FIG. 19, the gripper of the bayonet coupling is configured to be a radially projecting pin 90, 92 that is inclined upward. Said pin 90, 92 is longer than the comparable pin 26, 28 of FIG. 1.

Once the rod 24 has been placed into the receiving slot 22, the ring element 18 is also inserted in an axial direction into the receiving slot 22. The pins 90, 92 are thereby oriented so as to enter the entrance 30. Now, the operating surgeon must push the ring element 18 onto the rod 24, thereby exerting an appropriate force so that the rod is pushed further into the receiving slot 22 and so that the pins 90, 92 reach the bottom of the entrance 30. Once this position is achieved, the ring element 18 can be pivoted an angle width so that the pins 90, 92 enter the holding element 32. Since the rod 24 is hereby biased, it exerts a permanent pressure onto the ring element 18. This means that with reference to the FIGS. 19 to 21 the ring element 18 is pushed upward. The pins 90, 92 are now implemented with such a length that they protrude from the holding element 32 and are also inclined upward according to the force acting on the ring element 18. Thanks to this incline of the pins 90, 92, the forces acting through the rod 24 onto the pins 90, 92 are decomposed into an axial and a radial component. The radial component thereby causes the holding ridges 14, 16 to be pushed inward. As a result, it is made certain that the ring element 18 is reliably fixed in the holding ridges 14, 16 even if subjected to large forces.

In another embodiment not here presented the pins are configured to be bent, again for pushing the holding ridges inward.

It is understood that the flank 80, 82 of the FIGS. 16 to 18 may also be configured to be inclined or bent.

Depending on the purpose of utilization, the rod 24 may for example be configured to be a connection rod, a distraction rod or a compression rod.

Figure 22:
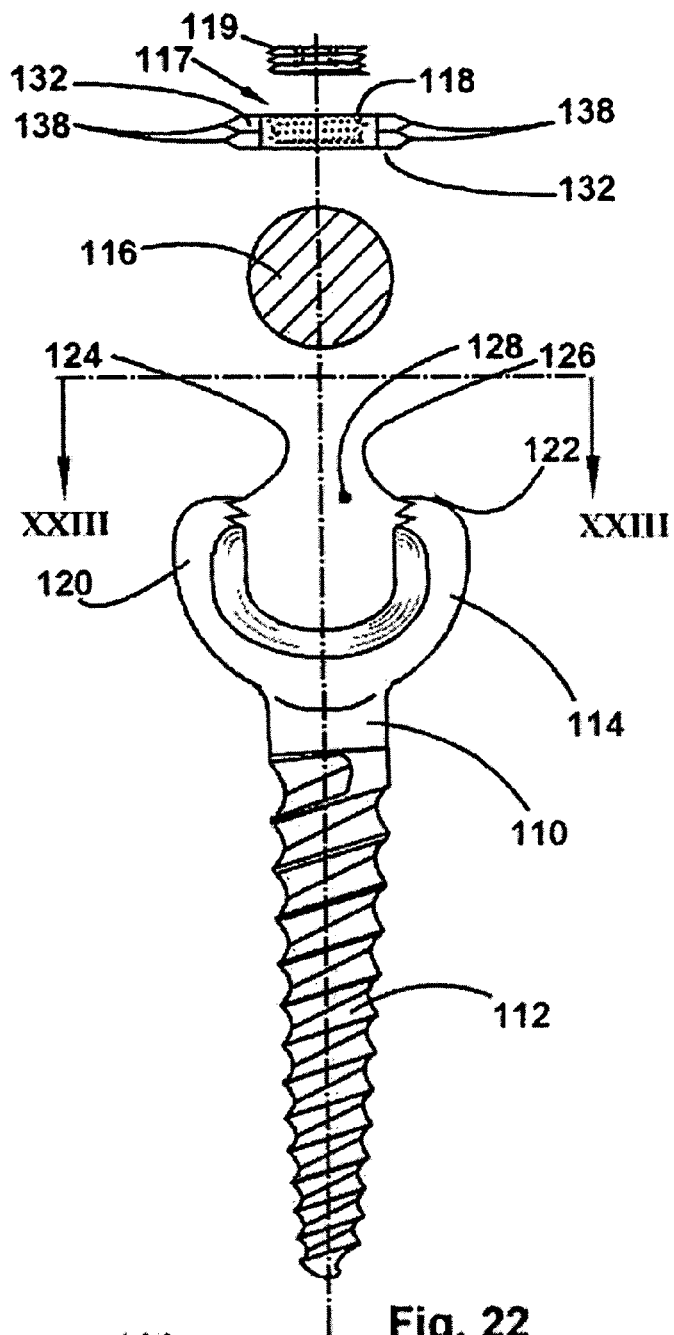
FIG. 22 is an exploded view of an eighth embodiment of an anchoring element of the invention with a rod.
Figure 23:
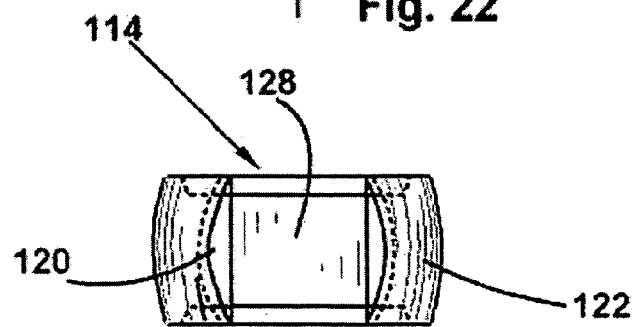
FIG. 23 is a top view of the holding device of the anchoring element of FIG. 22.
Figure 24:
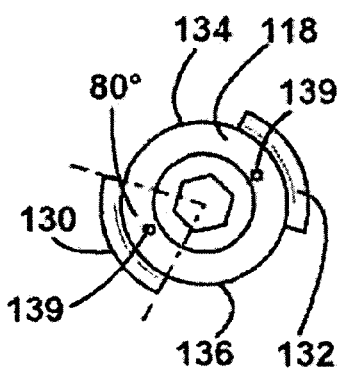
FIG. 24 is a top view of the securing element of the anchoring element of FIG. 22.

The FIGS. 22-24 are exploded views of another embodiment of an anchoring element of the invention. This screw-like anchoring element 110 includes a threaded shank which is screwable into the vertebral bone and on which there is attached a holding device 114 for fastening a rod 116. The anchoring element 110 also comprises a securing element 117 that includes a ring element 118 and a locking element 119 configured to be a grub screw. The securing element 117 is insertable into the holding device 114 and fixes the rod 116 in the holding device 114.

The holding device 114 is U-shaped in cross-section and includes two substantially parallely disposed holding ridges 120, 122. On a respective one of the sides of the holding ridges 120, 122 that are facing each other there is formed a partial thread 124, 126 that is implemented as a buttress thread.

The term buttress thread is meant to include, besides the buttress metric thread DIN 513, buttress threads having a slightly larger or slightly smaller flank angle, a flank angle of 0° or a negative flank angle as well as buttress threads in accordance with EP 885 598.

A slot 128 for receiving the rod 116 is formed in the holding device 114 between the holding ridges 120, 122. For fixing said rod, the securing element 117 is inserted with its ring element 118 into the partial thread 124, 126, thus pushing the rod 116 far into the receiving slot 128 and fixing it.

In order for the ring element 118 to be capable of reliably engaging into the partial threads 124, 126 of the holding ridges 120, 122, two thread portions 130, 132 are provided on the circumference of the ring element 118. As can be seen from the top view of FIG. 24, the thread portions 130, 132 are exactly opposite each other, entrance portions 134, 136 being formed between the respective thread portions 130, 132. Outside of the thread portions 130, 132, the circular ring element 118, which is circular in cross section, has a diameter which at most corresponds to the core diameter of the thread portions 130, 132. In the region of the thread portions 130, 132, two respective thread ribs 138 which form the respective thread portion 130, 132 are applied to the ring element 118. Like the partial threads 124, 126, the thread portions 130, 132 are also implemented as buttress threads. The thread portions 130, 132 extend over a circular segment of 80° and are disposed so as to be exactly opposite each other. Two tool mounts 139 into which a corresponding tool for screwing the ring element 118 into the holding device 114 is insertable are provided on a top side of the ring element 118. A locking element 119 that is configured to be a grub screw and is screwable independently of the ring element 118 is retained in the ring element 118, for example for final fixation of the rod. Said locking element 119 has a hexagonal wrench receiving recess 140 by means of which said locking element 119 can be firmly tightened.

Figures 25, 26:
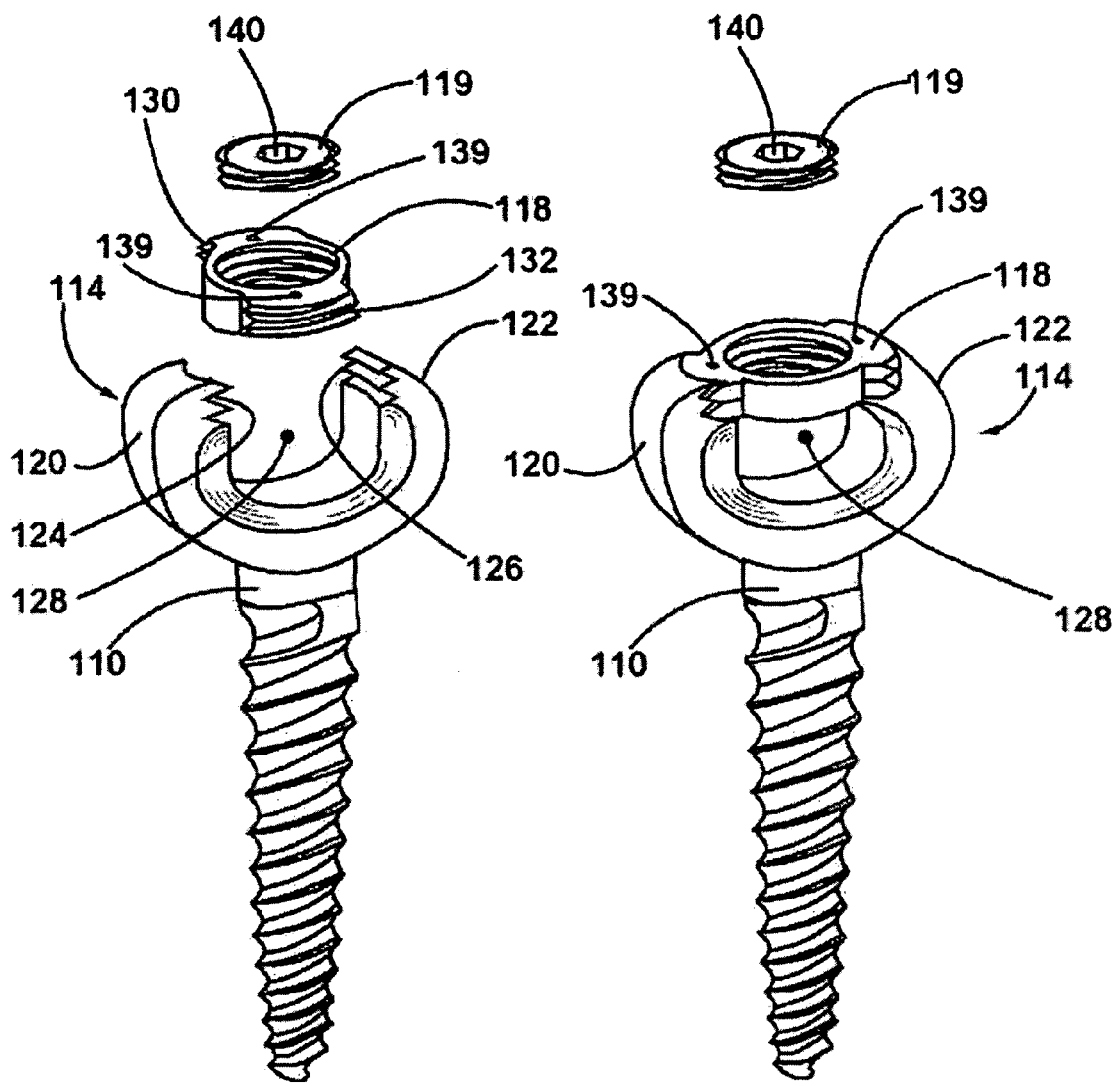
FIG. 25 is a perspective view of the anchoring element of FIG. 22, with the securing element being exploded or disassembled.
FIG. 26 is a perspective view of the anchoring element of FIG. 25, with the securing element being inserted in the holding device.

The FIGS. 25 and 26 perspectively illustrate the anchoring element 110 in two different positions, FIG. 25 showing the securing element 117 above the actual anchoring element 110 whereas the securing element 117 of FIG. 26 is shown inserted in the holding device 114. For inserting the securing element 117, the ring element 118 is taken hold of by tongs or a similar tool not here presented and is then axially inserted into the receiving slot 128 of the holding device 114. The ring element 118 is thereby oriented so that the entrance portions 134, 136 thereof are opposite the partial threads 124, 126 of the holding ridges 120, 122, whilst the thread portions 130, 132 are oriented in the direction of the receiving slot 128 in which position they protrude from the holding device 114. Once the securing element 118 has been inserted far enough into the receiving slot 128, it is pivoted 900. Now, the thread portions 130, 132 are inserted into the respective one of the partial threads 124, 126. In this condition, the securing element 118 fixes the rod in the holding device 114, the buttress thread preventing the holding ridges 120, 122 from being urged apart, thus making certain that the rod is reliably fastened in the anchoring element 110.

Figure 27:
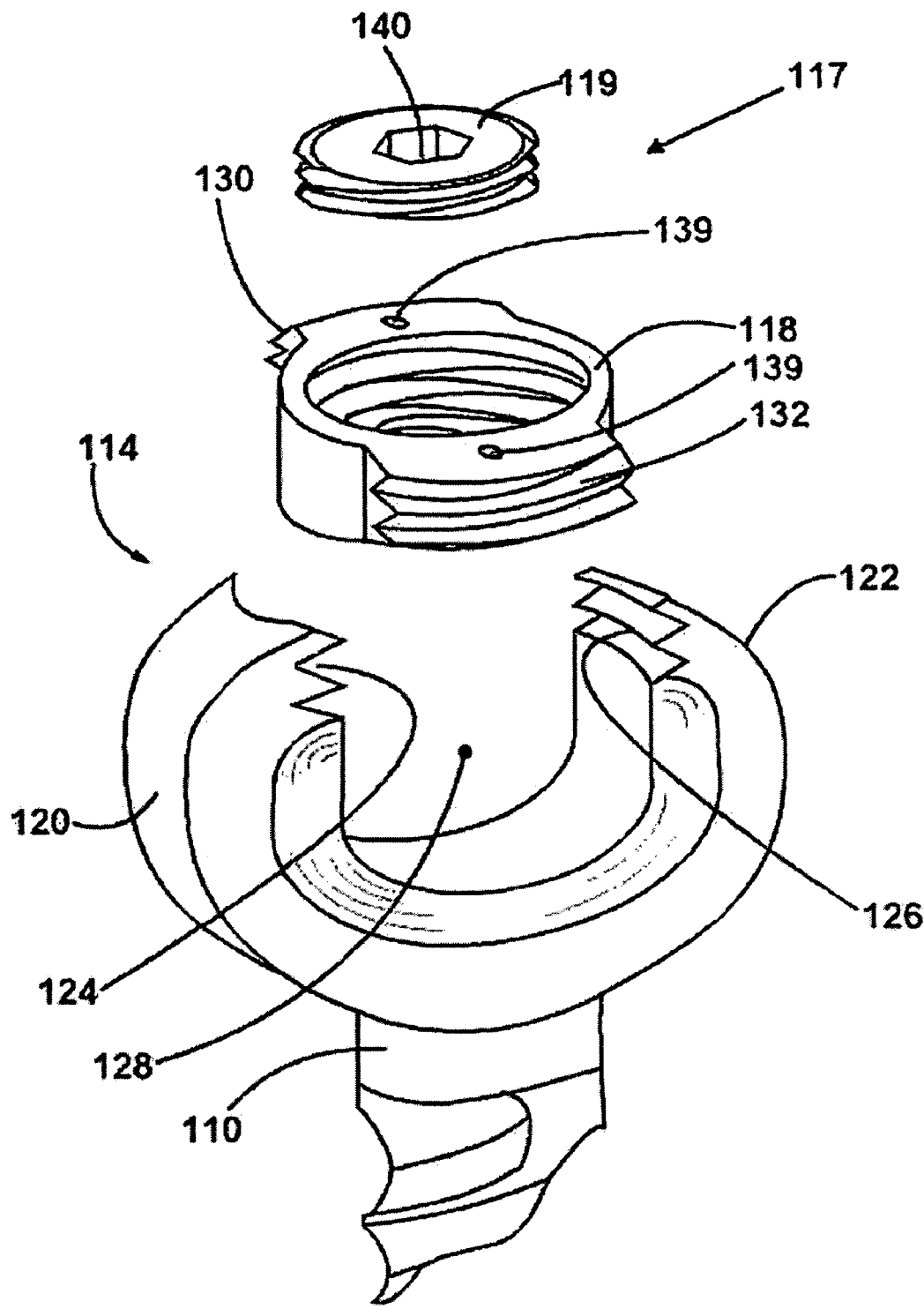
FIG. 27 is an enlarged detail of the anchoring element of FIG. 23.

From the enlarged detail view of FIG. 27 it can be readily seen that the thread ribs 138 of the thread portions 130, 132 are configured with at least one flattened front side. This makes it easier to insert the thread portions 130, 132 into the partial threads 124, 126 since the thread portions 130, 132 need only be approximately inserted into the partial thread 124, 125 in which they then move by themselves into the right position.

By reducing the thread of the ring element 118 to two confronting thread segments constituting nearly a one quarter threading, it is possible to guide the securing element 117 in the unthreaded region quickly and easily past the partial threads 124, 126 of the holding ridges 120, 122 and to insert it therein by a 90° rotation. This considerably facilitates the work of the operating surgeon and significantly reduces the duration of surgery.

Depending on the purpose of utilization, the rod 116 may for example be configured as a compression rod, a connection rod or a distraction rod.

In another embodiment not here presented there is provided that one partial thread 124 and/or one partial thread 126 is/are abutting so that the ring element 118 does not inadvertently expand too much, falling out of the holding device 114.

The FIGS. 28 to 30 illustrate still another embodiment of an anchoring element 150 of the invention which differs from the first embodiment by the design of the holding device 152 and by a ring element 154 configured in conformity therewith. As contrasted to the first embodiment, the holding ridges 156, 158 of the holding device 152 are dimensioned to be wider than the partial threads 160, 162 mounted in the holding ridges 156, 158 so that the partial threads 160, 162 do not extend as far as the respective edge of the holding ridges 156, 158 but end at a distance therefrom.

As best shown in FIG. 30, the ring element 154 is configured to have its entrance portions 164 and 166 provided with a comparably smooth convex surface so that it can be readily inserted into the receiving slot 128 between the holding ridges 156, 158 and rotated there until the thread portions 168, 170 engage the respective partial threads 160, 162 and reliably retain the ring element 154.

LISTING OF NUMERALS 10 threading shank
12 holding device
14 holding ridge
16 holding ridge
18 ring element
20 locking element
22 receiving slot
24 rod
26 pin
28 pin
30 entrance
32 holding element
34 internal thread
40 threaded shank
42 holding device
44 holding ridge
46 holding ridge
48 ring element
50 locking element
52 internal thread
54 receiving slot
56 pin
58 pin
60 entrance
61 entrance
62 holding element
63 holding element
66 holding element
68 widened portion
70 holding element
72 flank
74 flank
76 entrance
77 entrance
78 holding element
80 flank
82 flank
84 entrance
86 holding element
90 pin
92 pin
110 anchoring element
112 threaded shank 114 holding device
116 distraction or compression rod
117 securing element
118 ring element
119 locking element
120 holding ridge
122 holding ridge
124 partial thread
126 partial thread
128 receiving slot
130 thread portion
132 thread portion
134 entrance portion
136 entrance portion
138 thread rib
139 tool mount
140 hexagonal wrench receiving recess
150 anchoring element
152 holding device
154 ring element
156 holding ridge
158 holding ridge
160 partial thread
162 partial thread
164 entrance portion
166 entrance portion
168 thread portion
170 thread portion

I claim:

1. An anchoring element for fastening a rod of a device for adjusting a human or animal spine to a vertebral bone, said anchoring element having a holding device (12, 42) that is substantially U-shaped and includes two substantially parallely disposed holding ridges (14, 16, 44, 46), a rod (24) receiving slot (22, 54) being formed therein, and a securing element acting against the rod (24) accommodated in the receiving slot (22, 54), the securing element including a locking element (20, 50) and a ring element (18, 48), said ring element (18, 48) being mountable to the free end of the holding ridges (14, 16, 44, 46) by means of a single turn coupling system, the single turn coupling system being configured to be a bayonet coupling, said bayonet coupling including a slot-type or a groove-type receiving recess and a gripper engaging in said receiving recess, and the receiving recess including an axial entrance (32, 61, 76, 77, 84) and a tangential holding element (32, 62, 63, 66, 70, 78, 86), and the holding element (66) widens at its end.

2. The anchoring element as set forth in claim 1, characterized in that the entrance (30, 61, 76, 77, 84) is of a V-shape configuration type.

3. The anchoring element as set forth in claim 1, characterized in that the holding element (66, 70) is configured to slightly extend upward.

4. The anchoring element as set forth in claim 1, characterized in that the gripper is configured to be a pin (26, 28, 56, 58, 90, 92) or a flank (72, 74, 80, 82).

5. An anchoring element for fastening a rod of a device for adjusting a human or animal spine to a vertebral bone, said anchoring element having a holding device (12, 42) that is substantially U-shaped and includes two substantially parallely disposed holding ridges (14, 16, 44, 46), a rod (24) receiving slot (22, 54) being formed therein, and a securing element acting against the rod (24) accommodated in the receiving slot (22, 54), the securing element including a locking element (20, 50) and a ring element (18, 48), said ring element (18, 48) being mountable to the free end of the holding ridges (14, 16, 44, 46) by means of a single turn coupling system, the single turn coupling system being configured to be a bayonet coupling, and said bayonet coupling including a slot-type or a groove-type receiving recess and a gripper engaging in said receiving recess, and the substantially radially projecting gripper extends through the receiving recess and protrudes therefrom, said gripper being bent or inclined so that the gripper abutting on the holding ridge (14, 16) in the region of the holding element (32) pushes said holding ridge inward.

6. The anchoring element as set forth claim 5, characterized in that the receiving recess includes an axial entrance (30, 61, 76, 77, 84) and a tangential holding element (32, 62, 63, 66, 70, 78, 86).

7. The anchoring element as set forth in claim 5, characterized in that the ring element (18) is insertable into the receiving slot (22) and is mountable between the holding ridges (14, 16), the gripper of the bayonet coupling being mounted outside on the ring element (18) whilst the receiving recess is disposed in the holding ridges (14, 16).

8. The anchoring element as set forth in claim 5, characterized in that the ring element (48) surrounds the holding ridges (44, 46), the receiving recess being disposed in the ring element (48) whilst the gripper is mounted on the holding ridges (44, 46).

9. The anchoring element as set forth in claim 5, characterized in that a thread (34, 52) for receiving the locking element (20, 50) is provided in the ring element (18, 48).

* * * * *